US010058707B2

(12) United States Patent
Tol et al.

(10) Patent No.: US 10,058,707 B2
(45) Date of Patent: Aug. 28, 2018

(54) ELECTRONIC SYSTEM FOR A SYSTEM FOR NEURAL APPLICATIONS

(71) Applicant: Medtronic Bakken Research Center B.V., Maastricht (NL)

(72) Inventors: Jeroen Jacob Arnold Tol, Eindhoven (NL); Egbertus Johannes Maria Bakker, Wijk en Aalburg (NL)

(73) Assignee: Medtronic Bakken Research Center B.V., Maastricht (NL)

( * ) Notice: Subject to any disclaimer, the term of this patent is extended or adjusted under 35 U.S.C. 154(b) by 145 days.

(21) Appl. No.: 14/654,352

(22) PCT Filed: Dec. 18, 2013

(86) PCT No.: PCT/EP2013/077047
§ 371 (c)(1),
(2) Date: Jun. 19, 2015

(87) PCT Pub. No.: WO2014/095969
PCT Pub. Date: Jun. 26, 2014

(65) Prior Publication Data
US 2016/0367817 A1 Dec. 22, 2016

Related U.S. Application Data

(60) Provisional application No. 61/740,986, filed on Dec. 21, 2012.

(30) Foreign Application Priority Data

Dec. 21, 2012 (EP) .................................. 12199296

(51) Int. Cl.
*A61N 1/36* (2006.01)
*A61N 1/05* (2006.01)
(Continued)

(52) U.S. Cl.
CPC ...... *A61N 1/36142* (2013.01); *A61B 5/04001* (2013.01); *A61N 1/0526* (2013.01);
(Continued)

(58) Field of Classification Search
CPC .............. A61N 1/36142; A61N 1/0529; A61N 1/0526; A61N 1/08; A61N 1/0534; A61B 5/04001
See application file for complete search history.

(56) References Cited

U.S. PATENT DOCUMENTS 3,697,808 A * 10/1972 Lee ...................... A61B 5/0424
361/46
5,559,500 A * 9/1996 Kase ................ G01R 19/16538
323/315
(Continued)

FOREIGN PATENT DOCUMENTS

EP          2745873 A1    6/2014
WO     2010055453 A1    5/2010
(Continued)

OTHER PUBLICATIONS

U.S. Appl. No. 15/106,120, by Jeroen Jacob Arnold Tol et al., filed Jun. 17, 2016.
(Continued)

*Primary Examiner* — Michael Kahelin
(74) *Attorney, Agent, or Firm* — Shumaker & Sieffert, P.A.

(57) ABSTRACT

The present invention relates to an electronic system for a system for neural applications, comprising at least one first connector element and at least one second connector element, the first connector element being configured such that the electronic system is directly and/or indirectly connectable or connected to a controller which is at least configured to supply and/or provide and/or measure at least one voltage
(Continued)

and/or at least one current and/or at least one voltage waveform and/or at least one current waveform especially via one or more stimulation outputs and/or recording inputs, the second connector element being configured such that the electronic system is directly and/or indirectly connectable or connected to a lead for neural stimulation and/or recording, wherein the electronic system comprises at least one leakage current detection means configured such that a leakage current, especially a leakage current within and/or around the system for neural applications is detectable.

19 Claims, 8 Drawing Sheets

(51) Int. Cl.
  *A61N 1/08* (2006.01)
  *A61B 5/04* (2006.01)
(52) U.S. Cl.
  CPC ......... *A61N 1/0529* (2013.01); *A61N 1/0534* (2013.01); *A61N 1/08* (2013.01); *F04C 2270/041* (2013.01); *H01L 2924/0002* (2013.01)

(56) References Cited

U.S. PATENT DOCUMENTS

| | | | |
|---|---|---|---|
| 7,941,202 | B2 | 5/2011 | Hetke et al. |
| 2006/0173510 | A1 | 8/2006 | Besio et al. |
| 2006/0217782 | A1 | 9/2006 | Boveja et al. |
| 2007/0217121 | A1 | 9/2007 | Fu et al. |
| 2008/0119906 | A1 | 5/2008 | Starke |
| 2009/0259265 | A1 | 10/2009 | Stevenson et al. |
| 2010/0274319 | A1* | 10/2010 | Meskens .................. A61N 1/08 607/57 |
| 2011/0009917 | A1 | 1/2011 | Lavie |
| 2013/0070423 | A1 | 3/2013 | Iyer et al. |

FOREIGN PATENT DOCUMENTS

| | | |
|---|---|---|
| WO | 2012018631 A2 | 2/2012 |
| WO | 2014095997 A1 | 6/2014 |
| WO | 2015090633 A1 | 6/2015 |

OTHER PUBLICATIONS

International Search Report from International Application No. PCT/EP2013/077047, dated May 13, 2014, 4 pp.
International Preliminary Report on Patentability and Written Opinion from International Application No. PCT/EP2013/077047, dated Jun. 23, 2015, 6 pp.
Gosselin et al., "A Mixed-Signal Multichip Neural Recording Interface With Bandwidth Reduction," IEEE Transactions on Biomedical Circuits and Systems, vol. 3, No. 3, Jun. 2009, pp. 129-141.
Gosselin et al., "Circuits techniques and microsystems assembly for intracortical multichannel ENG recording," IEEE 2009 Custom Intergrated Circuits Conference (CICC), Sep. 13-16, 2009, pp. 97-104.

* cited by examiner

ELECTRONIC SYSTEM FOR A SYSTEM FOR NEURAL APPLICATIONS

The present invention relates to an electronic system for a system for neural applications, a lead for neural stimulation, a controller, an advanced lead can element, a neurostimulation and/or neurorecording system and a method of operating an electronic system.

Implantable neurostimulation devices have been used for the past ten years to treat acute or chronic neurological conditions. Deep brain stimulation (DBS), the mild electrical stimulation of sub-cortical structures, belongs to this category of implantable devices, and has been shown to be therapeutically effective for Parkinson's disease, Dystonia, and Tremor. New applications of DBS in the domain of psychiatric disorders (obsessive compulsive disorder, depression) are being researched and show promising results. In existing systems, the probes are connected to an implantable current pulse generator.

Currently, systems are under development with more, smaller electrodes in a technology based on thin film manufacturing. These novel systems consist of a lead made from a thin film based on thin film technology, as e.g. described in WO 2010/055453 A1. The thin film leads are fixed on a stylet material to form a probe. These probes will have multiple electrode areas and will enhance the precision to address the appropriate target in the brain and relax the specification of positioning. Meanwhile, undesired side effects due to undesired stimulation of neighbouring areas can be minimized.

Leads that are based on thin film manufacturing are e.g. described by U.S. Pat. No. 7,941,202 and have been used in research products in animal studies.

Implantable stimulation devices like e.g. systems for neural stimulation or Deep Brain Stimulation need to prevent leakage currents in order to prevent an unwanted application of current, especially DC current to the tissue of a patient. Such an unwanted application of current, especially DC current to the tissue of a patient is potentially harmful and should be prevented.

It is therefore an object of the present invention, to improve an electronic system for a system for neural applications, a lead for neural stimulation, a controller, an advanced lead can element, a neurostimulation and/or neurorecording system and a method of operating an electronic system, in particular in that a leakage current may be detected and e.g. following to that the system for neural applications may be switched into a safe state.

The above object is solved according to the present invention by an electronic system according to claim 1.

Accordingly, the present invention is based on the idea to provide an electronic system for a system for neural applications comprising at least one first connector element and at least one second connector element, wherein the first connector element is configured such that the electronic system is connectable or connected to a controller. The controller is configured to provide at least one electrical signal via one or more stimulation outputs. The second connector element is configured such that the electronic system is connectable or connected to a lead for neural stimulation, wherein the electronic system comprises at least one leakage current detection means. The leakage current detection means is configured such that a leakage current is detectable and/or preventable. Further, the electronic system is configured such that by design the at least one electrical signal provided via the one or more stimulation outputs has a substantially zero DC content or by design has a DC current that is inherently limited to substantially zero.

Moreover, the present invention is based on the idea to provide an electronic system for a system for neural applications comprising at least one first connector element and at least one second connector element. The first connector element is configured such that the electronic system is connectable or connected to a controller which is at least configured to measure at least one electrical signal via one or more recording inputs. The second connector element is configured such that the electronic system is connectable or connected to a lead for neural recording. Further, the electronic system comprises at least one leakage current detection means, wherein the at least one leakage current detection means is configured such that a leakage current is detectable and/or preventable. The electronic system is also configured such that the at least one electrical signal is monitored in order to detect the presence of a leakage current.

A further aspect of the present invention concerns a combination of the above-mentioned electronic systems. That is, the present invention is based on the idea to provide an electronic system that has the features of each of the electronic systems mentioned above. Accordingly, an electronic system for a system for neural applications is provided, comprising at least one first connector element and at least one second connector element, the first connector element being configured such that the electronic system is directly and/or indirectly connectable or connected to a controller which is at least configured to supply and/or provide and/or measure at least one voltage and/or at least one current and/or at least one voltage waveform and/or at least one current waveform especially via one or more stimulation outputs and/or recording inputs, the second connector element being configured such that the electronic system is directly and/or indirectly connectable or connected to a lead for neural stimulation and/or recording, wherein the electronic system comprises at least one leakage current detection means, wherein the at least one leakage current detection means is configured such that a leakage current is detectable.

Especially, a leakage current within and/or around the system for neural applications may be detectable.

By this, the advantage is achieved that leakage current, especially a leakage current within and/or around the system for neural applications may be detectable and following to that suitable measures and alerts are possible. In particular, it is possible after the detection of a leakage current to switch the electronic system or the system for neural applications into a safe operation state.

It is to be noted that the connection between the electronic system and the controller may be direct or indirect. In other words, the first connector element may be configured such that the electronic system is directly and/or indirectly connectable or connected to the controller. The electrical signal that is provided, supplied and/or measured by the controller may be a voltage and/or a current and/or a voltage waveform and/or a current waveform. The aforementioned features apply to all embodiments of the present invention.

Generally, the controller may have different functions. On the one hand, the controller may be configured to provide or supply the electrical signal, e.g. a voltage or current. On the other hand, the controller may be configured to measure the electrical signal. It is also possible to provide a controller that is adapted to perform both functionalities, i.e. supplying and measuring the electrical signal.

Moreover, it is to be noted that the electronic system may be configured to monitor the at least one electrical signal continuously and/or intermittently.

The electronic system may be an electronic system for a system for neural applications or, more specifically for brain applications, preferably for a neurostimulation and/or neurorecording system. Such a neurostimulation and/or neurorecording system may be e.g. a DBS system.

The lead may e.g. comprise at least one thin film, whereby the thin film comprises a proximal end and a distal end, the lead further comprising a plurality of electrodes on the distal end of the thin film.

The thin film may include at least one electrically conductive layer, preferably made of a biocompatible material. The thin film may be assembled to the carrier and further processed to constitute the lead element. The thin film for a lead is preferably formed by a thin film product having a distal end, a cable with metal tracks and a proximal end. The distal end of the thin film may be forming a part of the distal end of the lead or merely the distal end of the lead.

The distal end of the lead may be the end of the lead, which is in the implanted state of the lead the remote end of the lead with regard to the body surface area. In particular, in case of a lead for brain application, the distal end of the lead is the lower end of the lead, which is remote to the burr-hole of the skull, through which the lead is implanted.

The Advanced Lead Can element may comprise electronic means to address the plurality of electrodes and at least one Advanced Lead Can connecting means. Further, the Advanced Lead Can element may be hermetically or merely hermetically sealed and may comprise electronic means to address the plurality of electrodes on the distal end of the thin film, which is arranged at the distal end and next to the distal tip of the lead. The plurality of electrodes may comprise more than 5-10 electrodes, e.g. 16 or 32 electrodes or in preferred embodiments e.g. 64 electrodes or more. The electrodes may be arranged such that the electrodes are merely evenly distributed arranged all over the distal end of the lead.

For example, it is possible that the electronic system is configured such that the at least one voltage and/or at least one current and/or at least one voltage waveform and/or at least one current waveform is directly and/or indirectly continuously and/or intermittently monitored, especially continuously monitored, in order to detect the presence of a leakage current. So, in particular the electronic system is capable to monitor during stimulation, especially, but also during recording, especially during neurorecording and to detect leakage current.

For example, during a neural recording mode, no signal may be provided and the signal source is the tissue adjacent to the system for neural applications. However, even in such a situation a leakage current detection is possible by monitoring the recorded waveforms and/or exceptional and/or unexpected signals.

Furthermore, it is possible that by design the at least one voltage and/or at least one current and/or at least one voltage waveform and/or at least one current waveform provided via the one or more stimulation outputs has a substantially zero DC content or by design has a DC current that is inherently limited to substantially zero by design.

In particular, if by design the at least one voltage and/or at least one current and/or at least one voltage waveform and/or at least one current waveform provided via the one or more stimulation outputs has a substantially zero DC content or its DC current is inherently limited to substantially zero by design, no monitoring of the at least one voltage and/or at least one current and/or at least one voltage waveform and/or at least one current waveform is necessary. However, the monitoring can be provided for redundancy reasons.

Moreover, it is possible that the electronic system comprises at least one integrated passive device.

Integrated passive devices (IPD's) "or Integrated Passive Components (IPC's)" are attracting an increasing interest due to constant needs e.g. of handheld wireless devices to further decrease in size and cost and increase in functionality. Many functional blocks such as impedance matching circuits, harmonic filters, couplers and baluns and power combiner/divider can be realized by integrated passive devices technology. Integrated passive devices are generally fabricated using standard wafer fab technologies such as thin film and photolithography processing. Integrated passive devices can be designed as flip chip mountable or wire bondable components and the substrates for integrated passive devices usually are thin film substrates like silicon, alumina or glass.

DC blocking capacitors are often applied in implantable medical devices such as system for neural application in order to prevent e.g. DC leakage currents. Those and other passive components can be integrated on an integrated passive device, for example, to save precious implant volume and/or increase component reliability, which becomes attractive if many passives are needed. However, if the IPD fails, the DC voltage that is needed to bias the integrated passive device substrate can give rise to tissue leakage current. For example, if an integrated passive device with DC blocking capacitors is directly connected to e.g. a stimulation and/or recording electrode lead, an integrated passive device failure might short the integrated passive device substrate to one or more lead electrodes directly. This failure might lead to unwanted and potentially hazardous tissue DC leakage current. Advantageously, due to the use or provision of a leakage current detection means the integrated passive device can be biased safely.

It is possible that the integrated passive device comprises one or more stimulation inputs and/or recording outputs and/or at least one bias voltage input and/or one or more filtered stimulation outputs and or/recording inputs, especially wherein the in- and/or output of the integrated passive device is connected to the filtered out and/or input via at least one capacitor, and/or that the integrated passive device comprises a substrate and at least one passive electronic component which is arranged on and/or in the substrate.

The filtering can be provided by any means which is/are capable to provide a filtering. In particular, a filtering can be provided by any passive means or passive network.

Furthermore, it is possible that the integrated passive device comprises only one or more passive electronic components, especially at least one capacitor and/or at least one diode and/or at least one substrate terminal, further especially only capacitors and/or diodes and/or at least one substrate terminal.

Moreover, the electronic system comprises exemplarily at least one biasing means.

For correct functioning of the integrated passive, the common substrate may be to be biased with a voltage that is lower than the lowest voltage ever appearing on the in- and/or output terminals of the integrated passive device so that all component-substrate junctions remain reversed biased during normal operation. Otherwise unwanted substrate currents are injected into the integrated passive device, and therefore, into the integrated passive device components. Thus the integrated passive device should be provided with a DC voltage to bias its substrate correctly. Especially diodes of the integrated passive device may be biased, respectively reverse biased.

Again, if by design the at least one voltage and/or at least one current and/or at least one voltage waveform and/or at least one current waveform provided via the one or more stimulation outputs has a substantially zero DC content or its DC current is inherently limited to substantially zero by design, no monitoring of the at least one voltage and/or at least one current and/or at least one voltage waveform and/or at least one current waveform is necessary. If, e.g. due to a hardware failure a shortage exists and DC voltage to bias the integrated passive device may create a leakage current, this leakage current may be detected by the leakage current detection means quite easily due to the fact that the at least one voltage and/or at least one current and/or at least one voltage waveform and/or at least one current waveform provided via the one or more stimulation outputs has a substantially zero DC content or by design has a DC current that is inherently limited to substantially zero by design. However, the monitoring can be provided for redundancy reasons.

It is possible that the biasing means comprises at least one bias voltage output, which is connected and/or connectable to the bias voltage input of the integrated passive device, wherein especially the bias voltage input of the integrated passive device is connected to the substrate terminal.

Moreover, it is possible that the leakage current detection means is configured such that a leakage current is detected by directly and/or indirectly measuring the current of the bias voltage output, in particular by measuring a time-averaged current of the bias voltage output, especially by detecting whether a time-averaged current of the bias voltage output is above a predetermined threshold.

In particular, a measuring can be provided by e.g. a current limiting means like a current limiter, which is configured such that the current passing the current limiter is limited. So, also a measuring of e.g. the current is provided. An example of an indirect measuring could be an indirect detection of leakage current via a bias control mechanism that incorporates feedback.

It is possible that the leakage current detection means is configured such that a leakage current is detected by measuring a change in the voltage of the bias voltage output, in particular by measuring a time-averaged change of the bias voltage output, preferentially by detecting whether change and/or a time-averaged change of the bias voltage output is above a predetermined threshold.

The term above a predetermined threshold is to be interpreted in an absolute sense and could be e.g. a positive or negative voltage value.

Further, it is possible that the leakage current detection means is configured such that currents, of the one or more stimulation outputs and/or recording inputs are measurable or measured and/or that electronic system is configured to suspend directly and/or indirectly the stimulation and/or recording, especially the providing of at least one voltage and/or at least one current and/or at least one voltage waveform and/or at least one current waveform, if a leakage current is detected.

Especially, the currents may be time-averaged currents.

Moreover, the present invention relates to a lead for neural stimulation with the features of claim 11. Accordingly, a lead for neural stimulation is provided comprising at least one electronic system for a system for neural applications according to any of claims 1 to 10.

Furthermore, the present invention relates to a controller with the features of claim 12. Accordingly, a controller is provided, comprising at least one electronic system for a system for neural applications according to any of claims 1 to 10.

Especially, the controller may be an implantable pulse generator being capable to supply and/or provide and/or measure at least one voltage and/or at least one current and/or at least one voltage waveform and/or at least one current waveform especially via one or more stimulation outputs and/or recording inputs.

Moreover, the present invention relates to an advanced lead can element with the features of claim 13. Accordingly, an advanced lead can element is provided comprising at least one electronic system for a system for neural applications according to any of claims 1 to 10.

Furthermore, the present invention relates to a neurostimulation and/or neurorecording system with the features of claim 14. Accordingly, a neurostimulation and/or neurorecording system is provided, especially a deep brain stimulation (DBS) system, comprising at least one electronic system for a system for neural applications according to any of claims 1 to 10 and/or comprising at least one lead according to claims 11 and/or comprising at least one controller according to claim 12 and/or comprising at least one advanced lead can element according to claim 13.

Moreover, the present invention relates to a method of operating an electronic system for a system for neural applications, comprising at least the steps:

providing and/or measuring one or more stimulation and/or at least one recording signal and a bias voltage to an integrated passive device;

filtering the one or more stimulation and/or recording signals on the integrated passive device especially to remove DC components; and detecting a leakage current by measuring a current of the provided bias voltage and/or a change in bias voltage;

especially wherein the electronic system is an electronic system according to any of claims 1 to 10 or the electronic system is configured such that the functionality of the electronic system according to any of claims 1 to 10 is provided.

Further details and advantages of the present invention shall be described hereinafter with respect to the drawings.

Figure 1:
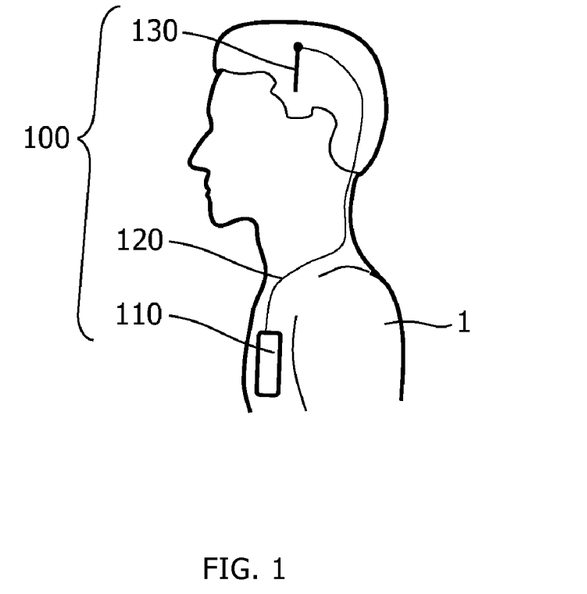
FIG. 1: a schematical drawing of a neurostimulation system for deep brain stimulation (DBS)

A possible embodiment of a neurostimulation system 100 for deep brain stimulation (DBS) is shown in FIG. 1. The neurostimulation system 100 comprises at least a controller 110 that may be surgically implanted in the chest region of a patient 1, typically below the clavicle or in the abdominal region of a patient 1. The controller 110 can be adapted to supply the necessary voltage and/or current pulses. The typical DBS system 100 may further include an extension wire 120 connected to the controller 110 and running subcutaneously to the skull, preferably along the neck, where it terminates in a connector. A DBS lead arrangement 130 may be implanted in the brain tissue, e.g. through a burr-hole in the skull.

Figure 2:
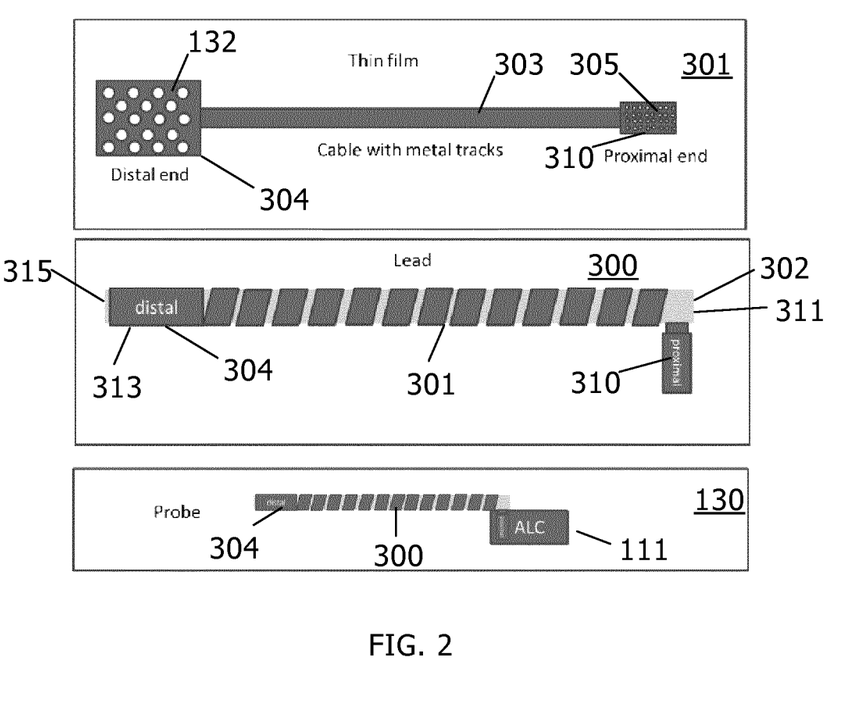
FIG. 2: a further schematical drawing of a probe neurostimulation system for deep brain stimulation (DBS) and its components.

FIG. 2 further illustrates a typical architecture for a Deep Brain Stimulation probe 130 that comprises a DBS lead 300 and an Advanced Lead Can element 111 comprising electronic means to address electrodes 132 on the distal end 304 of the thin film 301, which is arranged at the distal end 313 and next to the distal tip 315 of the DBS lead 300. The lead 300 comprises a carrier 302 for a thin film 301, said carrier 302 providing the mechanical configuration of the DBS lead 300 and the thin film 301. The thin film 301 may include at least one electrically conductive layer, preferably made of a biocompatible material. The thin film 301 is assembled to the carrier 302 and further processed to constitute the lead element 300. The thin film 301 for a lead is preferably formed by a thin film product having a distal end 304, a cable 303 with metal tracks and a proximal end 310. The proximal end 310 of the thin film 301 arranged at the proximal end 311 of the lead 300 is electrically connected to the Advanced Lead Can element 111. The Advanced Lead Can element 111 comprises the switch matrix of the DBS steering electronics. The distal end 304 comprises the electrodes 132 for the brain stimulation. The proximal end 310 comprises the interconnect contacts 305 for each metal line in the cable 303. The cable 303 comprises metal lines (not shown) to connect each distal electrodes 132 to a designated proximal contact 305.

Figure 3:
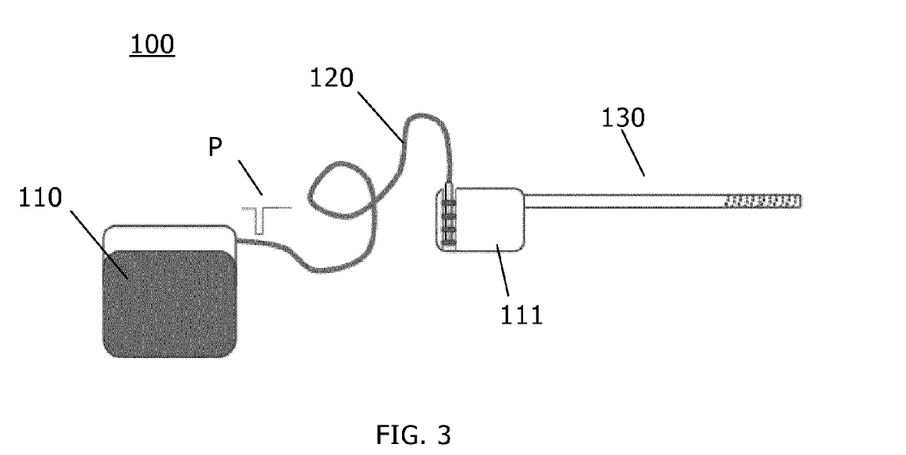
FIG. 3: a schematical drawing of a probe system according to the present invention.

FIG. 3 shows schematically and in greater detail an embodiment of a system 100 for brain applications, here for neurostimulation and/or neurorecording as a deep brain stimulation system 100 as shown in FIGS. 1 and 2. The probe system 100 comprises at least one probe 130 for brain applications with stimulation and/or recording electrodes 132, whereby e.g. 64 electrodes 132 can be provided on outer body surface at the distal end of the probe 130. By means of the extension wire 120 pulses P supplied by controller 110 can be transmitted to the Advanced Lead Can 111. The controller 110 can be an implantable pulse generator (IPG) 110.

In the implant industry, there is a continuous effort to reduce the size of implantables, which becomes even more important for modular implants with multiple modules such as a deep brain stimulation system 100 (DBS). Potential size reduction can also be traded for longer battery life time and a higher density of implant functions.

Figure 4:
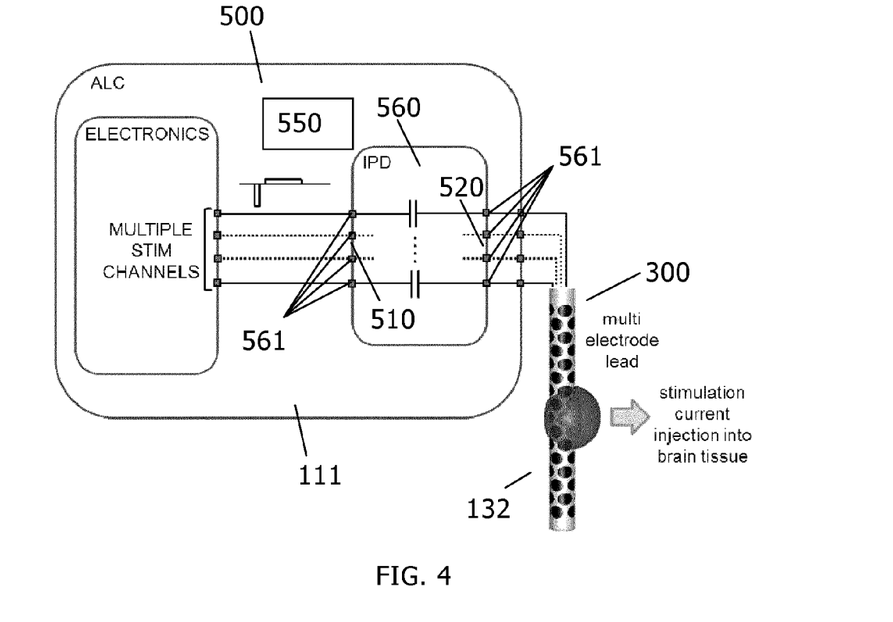
FIG. 4: a schematical drawing of an Advanced Lead Can with an integrated passive device according to the present invention.

Besides electronics architecture optimization, chip integration of electronic functions and components are key drivers to reduce implant size while simultaneously increasing implant functionality. An example is shown in FIG. 4, where an integrated passive device 560 is applied in-between the electronics in the Advanced Lead Can 111 and the multi-site lead 300. Each stimulation channel is AC coupled to one of the electrodes 132 on the lead 300 via a DC blocking capacitor and all DC blocking capacitors can be integrated on a single integrated passive device 560 die or can be spread over multiple integrated passive device 560 dies. The integrated passive device 560 comprises several stimulation inputs and/or recording outputs 561.

The higher the number of stimulation channels, where each Advanced Lead Can 111 stimulation channel addresses a single lead electrode, the larger the required number of DC blocking capacitors that one must fit in the Advanced Lead Can 111. Other passive and active components and chips increase the Advanced Lead Can 111 volume claim even further and an integrated passive device 560 for all or a majority of passive components, for example, the DC blocking capacitors shown in FIG. 4, enables further miniaturization of the Advanced Lead Can 111.

In the Advanced Lead Can 111 an electronic system 500 for a system for neural applications 100 is integrated, comprising at least one first connector element 510 and at least one second connector element 520.

The first connector element 510 is configured such that the electronic system 500 is indirectly connectable or connected to a controller 110 (not shown in FIG. 4; see FIG. 3) which is at least configured to supply and/or provide and/or directly and/or indirectly measure at least one voltage and/or at least one current and/or at least one voltage waveform and/or at least one current waveform especially via one or more stimulation outputs and/or recording inputs 561.

The second connector element 520 being configured such that the electronic system 500 is indirectly connectable or connected to a lead 300 for neural stimulation and/or recording, wherein the electronic system 500 comprises at least one leakage current detection means 550, wherein the at least one leakage current detection means 550 is configured such that a leakage current, especially a leakage current within and/or around the system for neural applications 100 is detectable.

Figure 5:
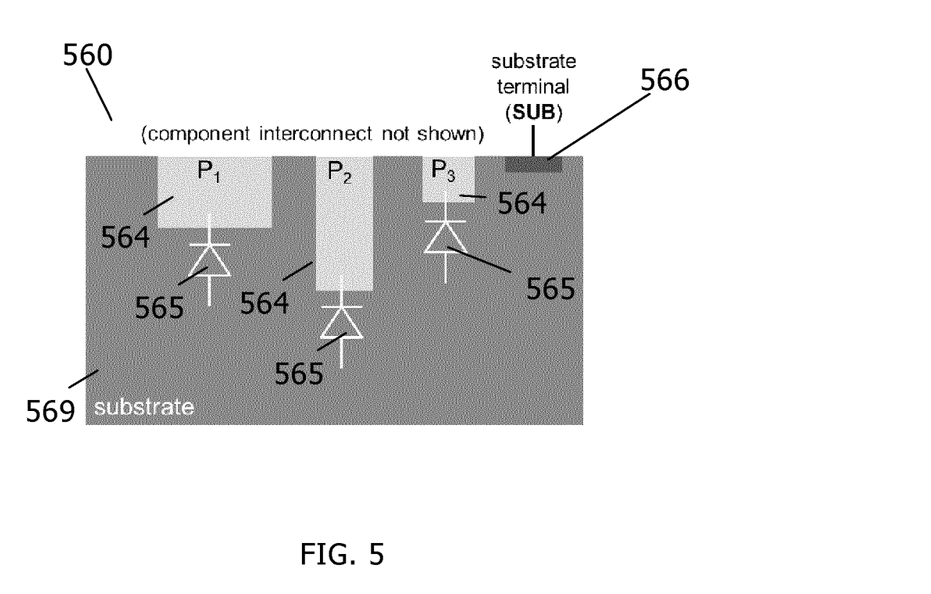
FIG. 5: a cross-section of a typical integrated passive device.

FIG. 5 show the cross-section of a typical integrated passive device 560 with multiple junction isolated passive components ($P_1, P_2, \ldots$) in a common substrate 569 having a substrate terminal 566. Each component is junction isolated from the common integrated passive device 560 substrate 569. The back-end interconnect layers and detailed view of each component has been omitted.

Figure 6:
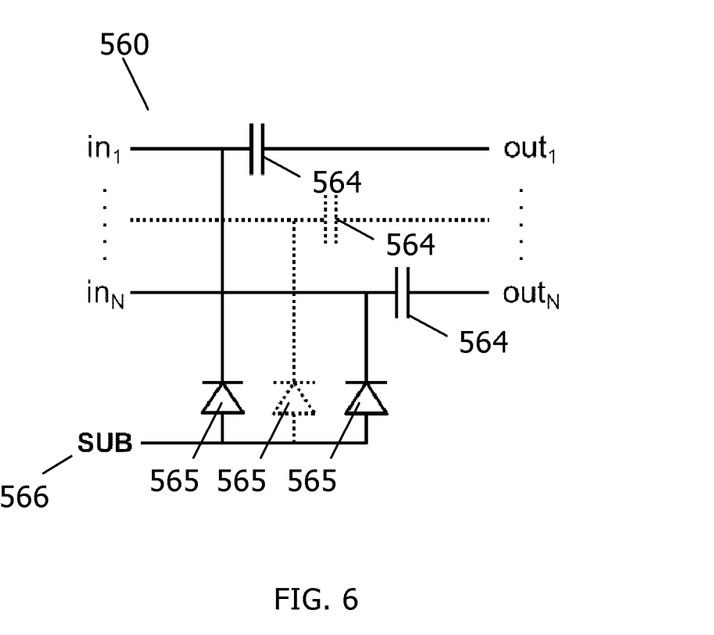
FIG. 6: an example of the equivalent electrical circuit of an integrated passive device.

As can be further seen in FIG. 6, the integrated passive device 560 with multiple junction isolated passive components ($P_1, P_2, \ldots$) may e.g. comprise as passive electronic components capacitors 564 and diodes 565.

FIG. 6 shows an example of the equivalent electrical circuit of an integrated passive device 560 where each component ($P_1, P_2, \ldots$) is an integrated capacitor 564. The integrated passive device 560 has N input terminals (in$_1$, . . . , in$_N$) and N output terminals (out$_1$, . . . , out$_N$) and a single substrate terminal 566 that connects to all component-substrate junctions simultaneously. Resistance as part of interconnect, components and substrate has been left out of the equivalent circuit for simplicity. So, FIG. 6 shows an integrated passive device 560 equivalent electrical circuit for an integrated capacitor array wherein the single substrate terminal 566 is connected to all component-substrate diodes 565 simultaneously. The substrate terminal bias voltage V$_{SUB}$ must comply with $$V_{SUB} \leq \min(V_{in1}, \ldots, V_{inN}).$$

For correct functioning of the integrated passive device 560, the common substrate needs to be biased with a voltage that is lower than the lowest voltage ever appearing on the input terminals of the integrated passive device 560 so that all component-substrate junctions remain reversed biased during normal operation. Otherwise unwanted substrate currents are injected into the integrated passive device 560, and therefore, into the integrated passive device 560 components 564, 565. Thus the integrated passive device 560 has to be provided with a DC voltage to bias its substrate correctly.

Figure 7:
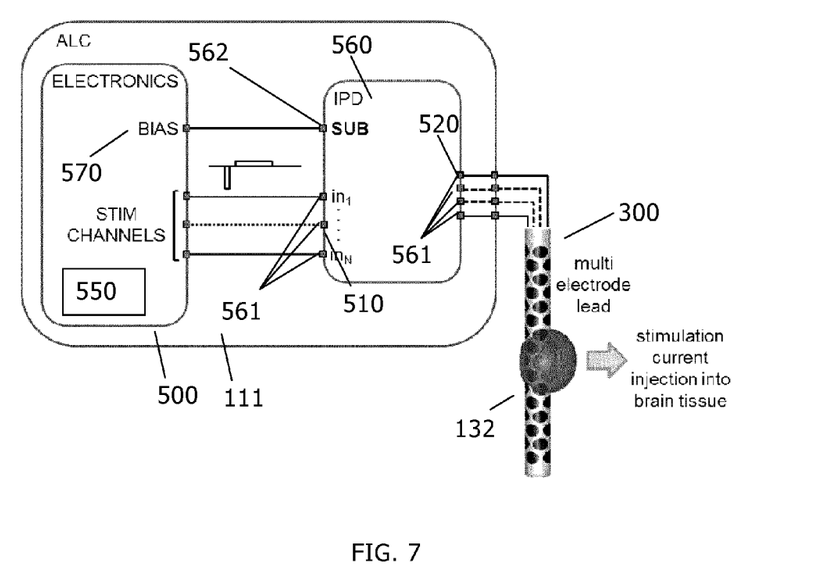
FIG. 7: a schematical drawing of an electronic system, which is integrated into the Advanced Lead Can.

In FIG. 7, this is done by the electronic system 500, which is integrated into the Advanced Lead Can 111.

The electronics of the Advanced Lead Can 111 provides by means of the biasing means 570 a DC voltage to the integrated passive device 560 to bias the integrated passive device 560 substrate correctly. If the integrated passive device 560 fails, the DC bias voltage might appear on the multi-electrode lead 300 directly.

One possible, but however very unlikely problem with providing a DC bias voltage to the integrated passive device 560 is that if the integrated passive device 560 fails, this voltage might appear on (one or more) integrated passive device 560 output pins directly, and therefore, on the electrodes 132 of the multi-electrode lead 300. This leads to DC (leakage) current flow through body tissue, in this example, the brains, which is regulatory not allowed as it poses a safety risk to the patient.

If the integrated passive device capacitor array is incorporated into the design to make sure that if the electronics fails, no DC tissue (leakage) current can ever arise due to a failure of the electronics, this problem shifts to the integrated passive device 560 when the substrate 569 integrated passive device 560 is connected with a DC bias voltage.

It should be noted that although FIG. 4 and FIG. 7 focus on the application of an integrated passive device 560 as part of the Advanced Lead Can 111, it is an example application of integrated passive device 560 use in an implantable.

Figure 8:
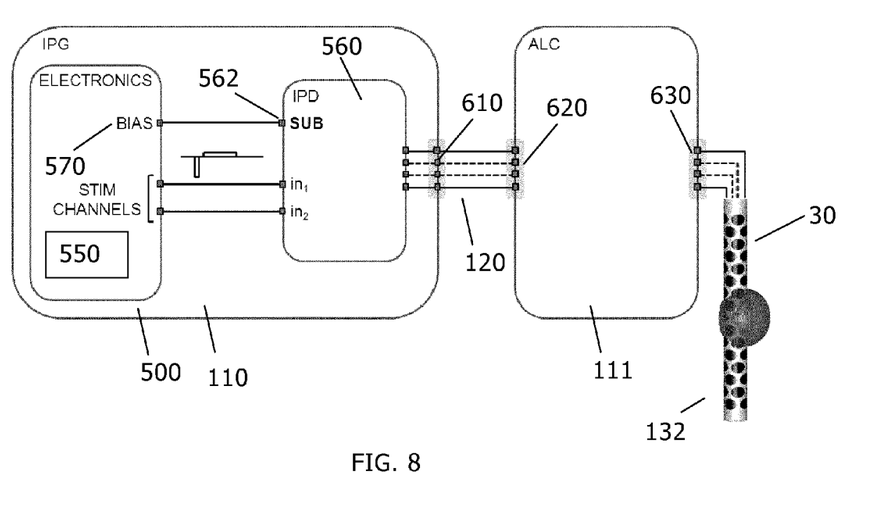
FIG. 8: a schematical drawing of an electronic system, which is integrated into the implantable pulse generator (IPG)

Another example is shown in FIG. 8, where an integrated passive device 560 is applied as part of the controller 110, here an implantable pulse generator (IPG) 110, in-between the implantable pulse generator (IPG) electronics and the integrated passive device connector 610 with attached interface cable 120 connecting the implantable pulse generator (IPG) 110 and the Advanced Lead Can 111.

The connectors 610, 620, 630 form inherent leakage paths to body tissue. Each implantable pulse generator (IPG) stimulation channel can address multiple lead electrodes 132 via a programmable cross-point switch matrix in the Advanced Lead Can 111.

The integrated passive device 560 within the implantable pulse generator (IPG) 110 can be an integrated capacitor array again to prevent potential tissue leakage currents if the implantable pulse generator (IPG) electronics fails. If the integrated passive device 560 were not present, those leakage currents can potentially flow into body tissue via, for example, the IPG and ALC connectors 610, 620 directly and/or via the cross-point switch matrix of the Advanced Lead Can 111 and lead connector 630 and/or lead indirectly (if e.g. no blocking capacitors are present in the Advanced Lead Can 111).

Finally, the use of an integrated passive device 560 to realize an array of integrated DC blocking capacitors is just taken as an example, although an important one, because integrated passive devices can be applied in many different cases where passives are involved. In addition, integrated passive devices can be part of other implant configurations than the ones shown in FIGS. 4 and 8.

Figure 9:
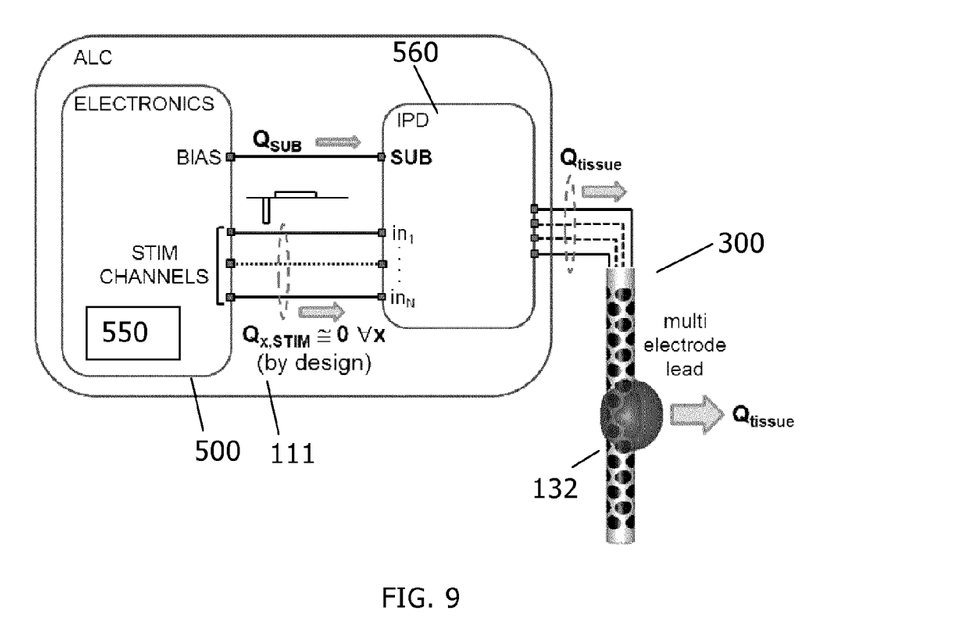
FIG. 9: a schematical drawing of an Advanced Lead Can with an integrated passive device according to the present invention and illustrating the integrated passive device charge balance.

FIG. 9 shows the integrated passive device 560 charge balance. By design, each stimulation channel injects no or almost no net charge into the body or $$Q_{x,STIM} \cong 0 \forall x \text{ with } x=1, \ldots, N$$

with $Q_{x,STIM}$ the net delivered stimulation charge of a channel in a stimulation period, x the stimulation channel number and N the total number of stimulation channels. Therefore, per Kirchoff's law, we can write $$Q_{tissue} \cong Q_{SUB}$$

with $Q_{tissue}$ the (net) charge injected into the body and $Q_{SUB}$ the (net) charge delivered by the bias source to the IPD substrate. Thus if the DC current of the bias source is (sufficiently) close to zero or $$Q_{SUB} \cong 0$$

no leakage current risk can arise, because $$Q_{tissue} \cong Q_{SUB} \cong 0$$

even in the event that the IPD fails and the IPD substrate is shorted or low-ohmically ("soft connection") connected to the lead electrodes directly.

In other words: The integrated passive device 560 charge balance reveals that the net charge injection $Q_{tissue}$ into body tissue equals the net delivered charge $Q_{SUB}$ of the IPD substrate bias voltage source or $Q_{tissue} \cong Q_{SUB}$ because each stimulation channel injects (almost) no net charge.

In the following, further embodiments are described which guarantee that the substrate bias source DC current is either continuously and/or intermittently monitored to detect directly or indirectly any change from (near) zero or its DC current is inherently limited to (near) zero by design.

Note that a non-zero bias source DC current cannot only arise because of DC leakage current flow into the body but other failures might also lead to a non-zero bias source DC current. For example, if (part of) the electronics fails, DC current could be drawn from the substrate bias source. Or if the amplitude of the stimulation pulses becomes (accidently) too high, forward biasing of component-substrate diodes leads to a non-zero DC substrate current.

However, with the technical teaching of the present invention, in particular with the embodiments of the present invention, tissue leakage current via an applied integrated passive device 560 becomes tolerant against (at least) single-faults appearing in either integrated passive device 560 or electronics. Finally, if a non-zero bias source DC current is detected that is not caused by DC current leaking into body tissue, it is still an indication that a fault has appeared in the implant's hardware (e.g. ALC) for which it is prudent to raise a flag and initiate further actions (diagnosis, interrupting or stopping stimulation, etc.).

In normal operation, the DC bias current $i_{SUB}$ is (close to) zero, because all integrated passive device component-substrate diodes are reversed biased. Any deviation from this (near) zero value implies that the integrated passive device charge balance, as explained with the help of 9, has been disturbed, for example, because of an integrated passive device failure.

Figure 10:
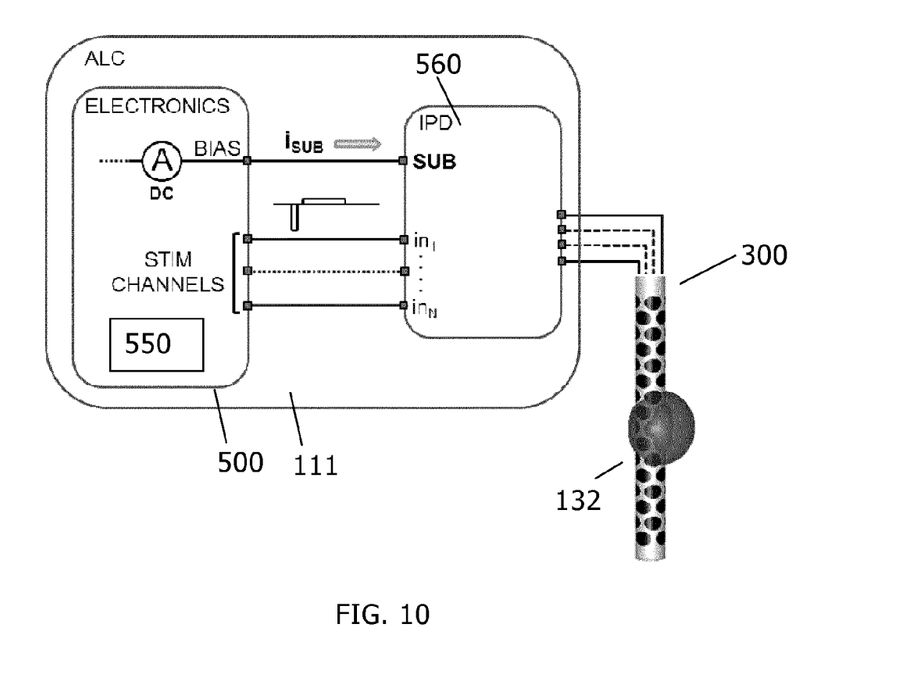
FIG. 10: a schematical drawing of an electronic system according to the invention, which is continuously monitoring the DC substrate current.

Thus, as depicted in FIG. 10, continuously and/or intermittently monitoring the DC substrate current $i_{SUB}$ is sufficient to prevent any DC leakage current flowing into body tissue, because the moment a deviation is detected, a flag can be raised and appropriate actions can be taken to stop the leaking current.

Different DC current detection methods can be applied. For example, a flag is raised if the DC current passes a pre-defined threshold value. Or one can monitor if the DC current (suddenly) deviates (e.g. 10%) with respect to a continuously measured moving average (e.g. over a 5 minutes interval) of the DC current.

So, the electronic system 500 continuously and/or intermittently monitors if the DC current of the substrate bias voltage source remains (sufficiently close to) zero. A detected deviation implies that the integrated passive device charge balance has been disturbed.

Figure 11:
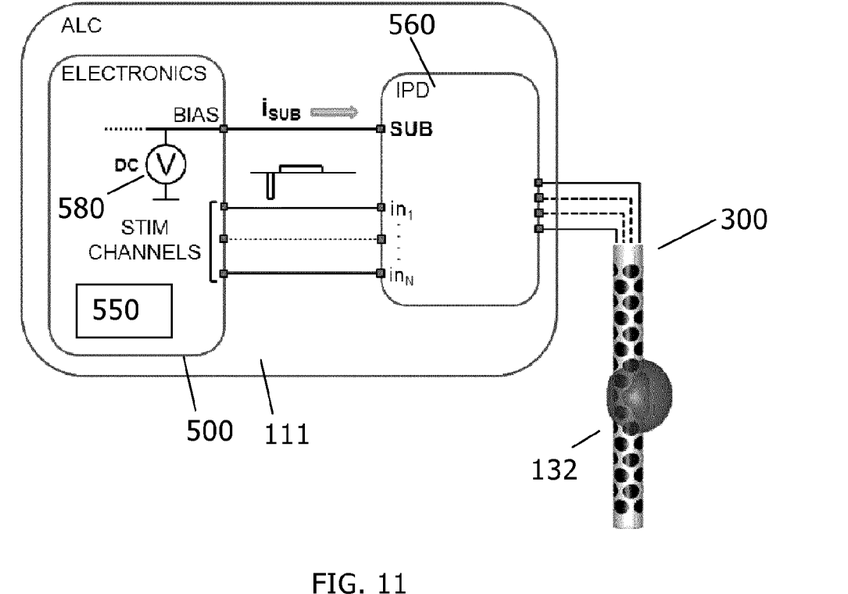
FIG. 11: a schematical drawing of an electronic system according to the invention, which is measuring changes in the DC voltage of the integrated passive device substrate bias source with a DC volt meter.

Another detection option is to measure changes in the DC voltage of the integrated substrate bias source with a DC volt meter 580 as is shown in FIG. 11. If the bias source has finite DC output impedance i.e. resistance, a change in substrate DC current translates into a change in bias voltage, which can be detected in a similar ways as outlined for the current measurement method.

So, a voltage measurement can be used to detect a deviation in the voltage of the bias source caused by a (sudden) change in its provided DC current.

It is also possible to monitor any change in DC substrate impedance i.e. resistance, for example, by simultaneous measurement of bias current and bias voltage i.e. a combination of FIG. 10 and FIG. 11. In addition, AC current, voltage or impedance measurements can be applied as an early warning of upcoming hardware failure.

Figure 12:
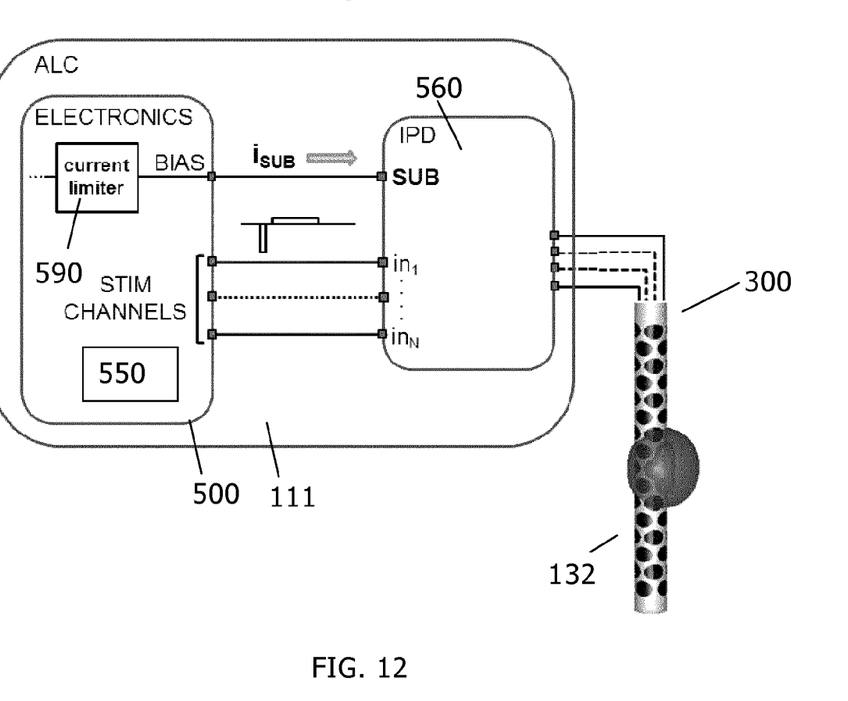
FIG. 12: a schematical drawing of an electronic system according to the invention comprising a current limiter.

The DC integrated passive device substrate current is by design (almost) zero if the integrated passive device substrate is biased correctly, and therefore, as shown in FIG. 12, one can insert a current limiter 590 into the bias line from the IPD to guarantee that, by design, the DC current provided by the bias source can never exceed a pre-determined limit, for example, a regulatory maximum leakage current limit (e.g. 100 nA). A flag can be raised when the current limit is exceeded.

The current limiter 590 can be a separate functional block but it can also be inherent in the design of the bias source, for example, when it is designed with high output impedance. Moreover, the current limiter 590 can be combined with the just presented current, voltage and/or impedance measurements.

An integrated passive device is a passive (multi-port) network by definition and no energy sources are contained in the integrated passive device. Therefore, if the biasing of the integrated passive device substrate is also done in passive way, no DC current can arise from the integrated passive device as we assume that each stimulation channel carries no DC current.

Figure 13:
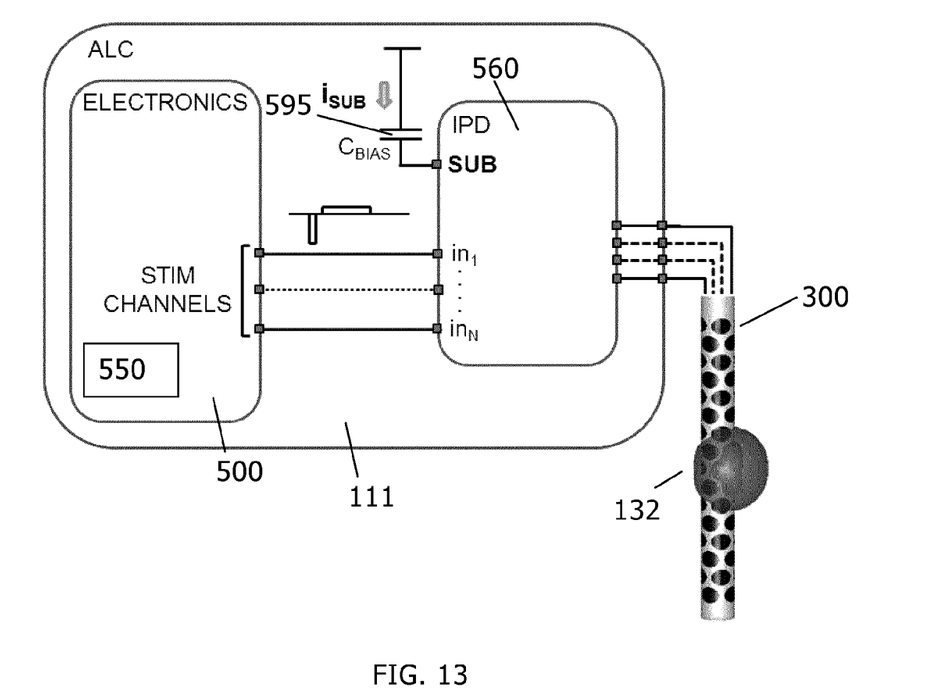
FIG. 13: a schematical drawing of an electronic system according to the invention being capable of biasing the substrate of the integrated passive device in a passive manner.

An example of biasing the substrate of the integrated passive device 560 in a passive manner is shown in FIG. 13, where a capacitor 595 is connected between the integrated passive device substrate terminal and for example ground. The electronics is now connected to a completely passive network and any failure of this network cannot lead to tissue leakage current by design, because the lines between electronics and integrated passive device carry (almost) DC free signals only.

Figure 14:
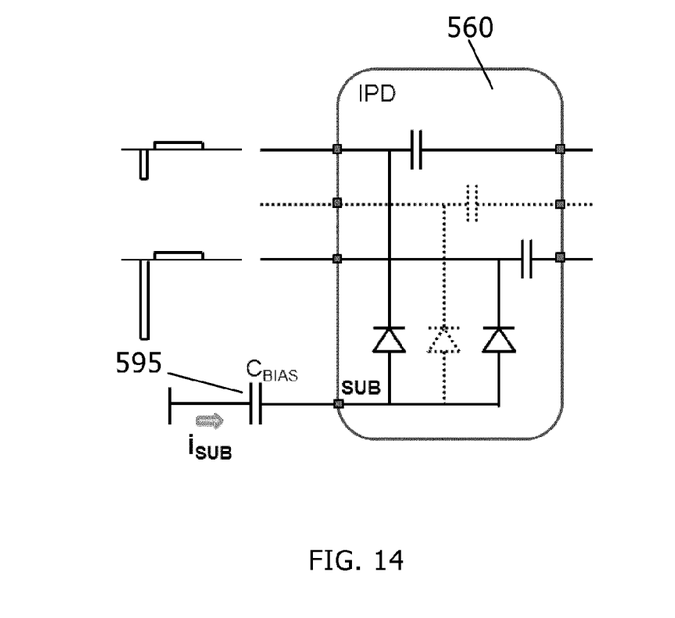
FIG. 14: a schematical drawing of an electronic system according to the invention having a peak detector capacitor.

The capacitor 595 $C_{BIAS}$ forms a peak detector with the component-substrate diodes as shown in FIG. 14. In this way, the substrate of the integrated passive device 560 is appropriately biased to the most negative voltage appearing on the stimulation channel lines. Thus the capacitor 595 is applied as an energy storage element.

Figure 15:
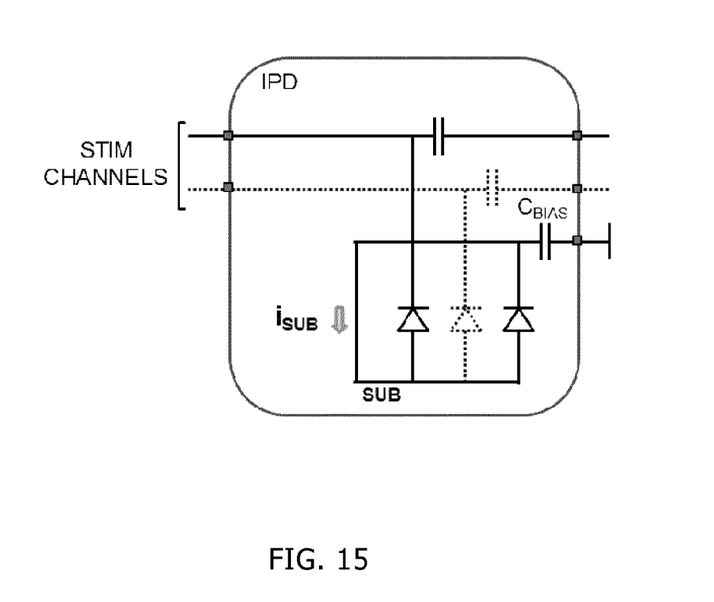
FIG. 15: a schematical drawing of an electronic system according to the invention, wherein a peak detector capacitor is part of the integrated passive device.

The capacitor 595 $C_{BIAS}$ can be part of the capacitor array of the integrated passive device 560 as shown in FIG. 15.

Figure 16:
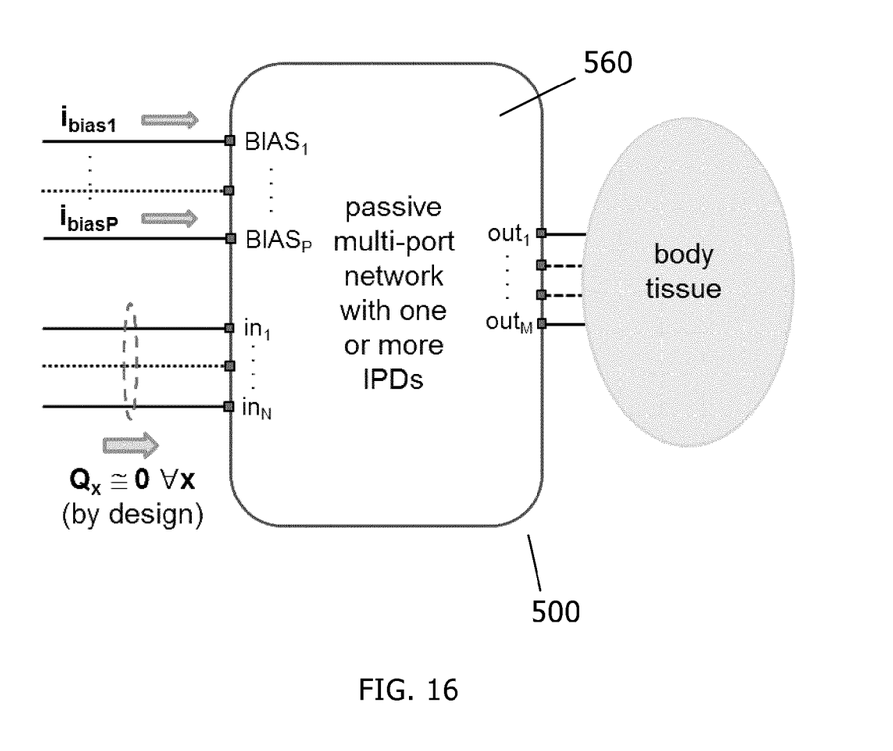
FIG. 16: a further schematical drawing of an electronic system according to the invention.

FIG. 16 shows a passive multi-port network with N charge balanced inputs, M outputs, which may be in direct contact with body tissue, and P bias points. All previously relayed concepts can be applied to one or more bias points ($BIAS_1, \ldots, BIAS_P$) of the passive multi-port to make sure that if the passive network fails, no DC current will flow through body tissue.

Finally note that the proposed methods cannot only be applied to prevent unwanted DC leakage currents. Detection of IPD (substrate) failure might also be beneficial when the appearance of a DC voltage on any of the in- and/or output terminals of the IPD, or the passive network containing an IPD, leads to a hazardous or unwanted situation, for example, due to exceeded breakdown voltage of attached circuitry.

This invention as exemplarily described above in connection with the embodiments shown in the Figures can be used in implantable medical devices of any kind that apply integrated passive devices whose substrate needs to be biased safely, for example, to prevent DC current flow through body tissue in case of hardware failure.

Explicitly disclosed, alternatively and/or together with the above mentioned technical teaching and invention, is an electronic system for a system for neural applications, especially a neurostimulation and/or neurorecording system, further especially a deep brain stimulation (DBS) system, comprising at least one integrated passive device.

In the context of the present invention, the following additional aspects are disclosed:

1. An electronic system (500) for a system for neural applications (100), especially a neurostimulation and/or neurorecording system (100), further especially a deep brain stimulation (DBS) system (100), comprising at least one first connector element (510) and at least one second connector element (520), the first connector element (510) being configured such that the electronic system (500) is directly and/or indirectly connectable or connected to a controller (110) which is at least configured to supply and/or provide and/or measure at least one voltage and/or at least one current and/or at least one voltage waveform and/or at least one current waveform especially via one or more stimulation outputs and/or recording inputs (110), the second connector element (520) being configured such that the electronic system (500) is directly and/or indirectly connectable or connected to a lead (300) for neural stimulation and/or recording, wherein the electronic system comprises at least one leakage current detection means (550), wherein the at least one leakage current detection means (550) is configured such that a leakage current, especially a leakage current within and/or around the system for neural applications (100) is detectable and/or preventable.

2. The electronic system (500) according to aspect 1, characterized in that
the electronic system (500) is configured such that the at least one voltage and/or at least one current and/or at least one voltage waveform and/or at least one current waveform is directly and/or indirectly continuously and/or intermittently monitored, especially continuously monitored, in order to detect the presence of a leakage current and/or that by design the at least one voltage and/or at least one current and/or at least one voltage waveform and/or at least one current waveform provided via the one or more stimulation outputs has a substantially zero DC content or by design has a DC current that is inherently limited to substantially zero.

3. The electronic system (500) according to aspect 1 or 2, characterized in that
the electronic system (500) comprises at least one integrated passive device (560).

4. The electronic system (500) according to aspect 3, characterized in that
the integrated passive device (560) comprises one or more stimulation inputs and/or recording outputs (561) and/or at least one bias voltage input (562) and/or one or more filtered stimulation outputs and or/recording inputs, especially wherein the in- and/or output (561) of the integrated passive device (560) is connected to the filtered out- and/or input (561) via at least one capacitor (564), and/or that the integrated passive device (560) comprises a substrate (569) and at least one passive electronic component (564, 565, 566) which is arranged on and/or in the substrate (569).

5. The electronic system (500) according to aspect 4, characterized in that
the integrated passive device (560) comprises only one or more passive electronic components (564, 565, 566), especially at least one capacitor (564) and/or at least one diode (565) and/or at least one substrate terminal (566), further especially only capacitors and/or diodes and/or at least one substrate terminal (566).

6. The electronic system (500) according to any one of the preceding aspects, characterized in that
the electronic system (500) comprises at least one biasing means (570).

7. The electronic system (500) according to aspect 6, especially according to aspects 5 and 6, characterized in that
the biasing means (570) comprises at least one bias voltage output, which is connected and/or connectable to the bias voltage input (562) of the integrated passive device (560), wherein especially the bias voltage input of the integrated passive device is connected to the substrate terminal (566).

8. The electronic system (500) according to any one of the preceding aspects, characterized in that
the leakage current detection means (550) is configured such that a leakage current is detected by directly and/or indirectly measuring the current of the bias voltage output, in particular by measuring a time-averaged current of the bias voltage output, especially by detecting whether a time-averaged current of the bias voltage output is above a predetermined threshold.

9. The electronic system (500) according to any one of the preceding aspects, characterized in that
the leakage current detection means (550) is configured such that a leakage current is detected by measuring a change in the voltage of the bias voltage output, in particular by measuring a time-averaged change of the bias voltage output, preferentially by detecting whether a change and/or a time-averaged change of the bias voltage output is above a predetermined threshold.

10. The electronic system (500) according to any one of the preceding aspects, characterized in that
the leakage current detection means (550) is configured such that currents, especially time-averaged currents, of the one or more stimulation outputs and/or recording inputs are measurable or measured and/or that electronic system (500) is configured to suspend directly and/or indirectly the stimulation and/or recording, especially the providing of at least one voltage and/or at least one current and/or at least one voltage waveform and/or at least one current waveform, if a leakage current is detected.

11. A lead (300) for neural stimulation comprising at least one electronic system for a system for neural applications (100) according to any of aspects 1 to 10.

12. A controller (110), especially an implantable pulse generator (110) comprising at least one electronic system for a system for neural applications (100) according to any of aspects 1 to 10.

13. An advanced lead can element (111) comprising at least one electronic system for a system for neural applications (100) according to any of aspects 1 to 10.

14. A neurostimulation and/or neurorecording system (100), especially a deep brain stimulation (DBS) system (100), comprising at least one electronic system (500) for a system for neural applications (100) according to any of aspects 1 to 10 and/or comprising at least one lead (300) according to aspect 11 and/or comprising at least one controller (110) according to aspect 12 and/or comprising at least one advanced lead can element (111) according to aspect 13.

15. A method of operating an electronic system (500) for a system for neural applications (100), comprising at least the steps:
providing and/or measuring one or more stimulation and/or at least one recording signal and a bias voltage to an integrated passive device (560);
filtering the one or more stimulation and/or recording signals on the integrated passive device (560) especially to remove DC components; and
detecting a leakage current by measuring a current of the provided bias voltage and/or a change in bias voltage;
especially wherein the electronic system (500) is an electronic system (500) according to any of aspects 1 to 10 or the electronic system (500) is configured such that the functionality of the electronic system (500) according to any of aspects 1 to 10 is provided.

The invention claimed is:
1. An electronic system for a system for neural applications, the electronic system comprising:
at least one first connector element configured to connect the electronic system to a controller, the at least one first connector element configured to receive at least one electrical signal from the controller via one or more stimulation outputs;
at least one second connector element configured to connect the electronic system to a lead configured to deliver neural stimulation;

an integrated passive device comprising a substrate and at least one passive electronic component arranged one of on or in the substrate;

a biasing circuit configured to provide a DC bias voltage to the substrate of the integrated passive device; and at least one leakage current detection circuit configured to measure at least one of a current of the bias voltage or a change in the DC bias voltage.

2. The electronic system of claim 1, wherein the integrated passive device electrically couples the at least one first connector element to the at least one second connector element.

3. The electronic system of claim 2, wherein the integrated passive device comprises:

one or more stimulation inputs, at least one bias voltage input, and one or more filtered stimulation outputs, the one or more stimulation inputs of the integrated passive device being connected to the filtered stimulation outputs via at least one capacitor.

4. The electronic system of claim 3, wherein the one or more passive electronic components comprises one or more of a capacitor, a diode, or a substrate terminal.

5. The electronic system of claim 1, wherein the biasing circuit comprises at least one bias voltage output connected to a bias voltage input of the integrated passive device.

6. The electronic system of claim 1, wherein the leakage current detection circuit is configured to measure a time-averaged current of a bias voltage output of the biasing circuit and detect a leakage current based on whether the time-averaged current of the bias voltage output is above a predetermined threshold.

7. The electronic system of claim 1, wherein the leakage current detection circuit is configured to measure a time-averaged change of a bias voltage output of the biasing circuit and detect a leakage current based on whether the change of the bias voltage output is above a predetermined threshold.

8. The electronic system of claim 1, wherein the leakage current detection circuit is configured to measure time-averaged currents of the one or more stimulation outputs, and wherein the electronic system is configured to suspend delivery of the neural stimulation if a leakage current is detected.

9. The electronic system of claim 1, further comprising the lead.

10. The electronic system of claim 1, further comprising the controller, wherein the controller comprises an implantable pulse generator.

11. The electronic system of claim 1, further comprising an advanced lead can element configured to house the at least first connector element, the at least one second connector element, the biasing circuit, and the at least one leakage current detection circuit, wherein the advanced lead can element is connectable to the controller and the lead.

12. The electronic system of claim 1, further comprising the lead, the controller, and at least one advanced lead can element.

13. The electronic system of claim 1, wherein the at least one electrical signal comprises at least one stimulation signal, and wherein the integrated passive device is configured to remove one or more DC components from the at least one stimulation signal to generate at least one filtered stimulation signal.

14. The electronic system of claim 13, wherein the electronic system is configured to deliver the at least one filtered stimulation signal to the lead via the at least one second connector element.

15. A method comprising:

receiving, by an integrated passive device and via at least one first connector element connected to one or more stimulation outputs, at least one electrical signal from a controller;

delivering, from the integrated passive device and via at least one second connector element connected to a lead, neural stimulation via the lead;

providing, via a biasing circuit, a DC bias voltage to a substrate of the integrated passive device, the integrated passive device comprising at least one passive electronic component arranged one of on or in the substrate; and measuring, by at least one leakage current detection circuit, at least one of a current of the bias voltage or a change in the DC bias voltage.

16. The method of claim 15, further comprising removing, by the integrated passive device, one or more DC components from the at least one electrical signal to generate at least one filtered stimulation signal, wherein delivering neural stimulation comprises delivering the at least one filtered stimulation signal.

17. The method of claim 15, wherein providing the DC bias voltage comprises providing the DC bias voltage from a bias voltage output to a bias voltage input of the integrated passive device, and wherein measuring the current of the DC bias voltage comprises measuring a time-averaged current of the bias voltage output and detecting a leakage current by detecting whether the time-averaged current of the bias voltage output is above a predetermined threshold.

18. The method of claim 15, wherein providing the DC bias voltage comprises providing the DC bias voltage from a bias voltage output to a bias voltage input of the integrated passive device, and wherein measuring the change in the bias voltage comprises measuring a time-averaged change of the DC bias voltage and detecting a leakage current by detecting whether the time-averaged change of the bias voltage output is above a predetermined threshold.

19. The method of claim 15, wherein:

the integrated passive device comprises one or more stimulation inputs, at least one bias voltage input, and one or more filtered stimulation outputs, the one or more stimulation inputs of the integrated passive device being connected to the filtered stimulation outputs via at least one capacitor; and the one or more passive electronic components comprises one or more of a capacitor, a diode, or a substrate terminal.

* * * * *